(12) United States Patent
Degrado et al.

(10) Patent No.: US 9,988,336 B2
(45) Date of Patent: Jun. 5, 2018

(54) GASEOUS F-18 TECHNOLOGIES (71) Applicant: MAYO FOUNDATION FOR MEDICAL EDUCATION AND RESEARCH, Rochester, MN (US)

(72) Inventors: Timothy R. Degrado, Rochester, MN (US); Huailei Jiang, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days. days.

(21) Appl. No.: 15/127,074

(22) PCT Filed: Mar. 18, 2015

(86) PCT No.: PCT/US2015/021215
§ 371 (c)(1),
(2) Date: Sep. 19, 2016

(87) PCT Pub. No.: WO2015/143019
PCT Pub. Date: Sep. 24, 2015

(65) Prior Publication Data
US 2017/0174606 A1    Jun. 22, 2017

Related U.S. Application Data (60) Provisional application No. 61/954,839, filed on Mar. 18, 2014.

(51) Int. Cl.
C07C 51/60 (2006.01)
A61K 51/04 (2006.01)

(52) U.S. Cl.
CPC .......... *C07C 51/60* (2013.01); *A61K 51/0402* (2013.01)

(58) Field of Classification Search
CPC .... C07C 51/60; A61K 51/0402; A61K 51/04; C07B 59/001
See application file for complete search history.

(56) References Cited

U.S. PATENT DOCUMENTS

| | | | | |
|---|---|---|---|---|
| 4,059,633 A * | 11/1977 | Childs | ........... | C07C 45/82 568/411 |
| 4,617,386 A | 10/1986 | Elmaleh et al. | | |
| 4,794,178 A | 12/1988 | Coenen et al. | | |
| 5,169,942 A | 12/1992 | Johnson et al. | | |
| 5,264,570 A | 11/1993 | Johnson et al. | | |
| 5,436,325 A | 7/1995 | Johnson et al. | | |
| 5,759,513 A | 6/1998 | Nakazawa | | |
| 5,808,020 A | 9/1998 | Ferrieri et al. | | |
| 5,932,178 A | 8/1999 | Yamazaki et al. | | |
| 6,172,207 B1 | 1/2001 | Damhaut et al. | | |
| 2007/0036716 A1 | 2/2007 | Casebier et al. | | |
| 2009/0247793 A1 | 10/2009 | Arstad | | |
| 2010/0069609 A1 | 3/2010 | Arstad | | |
| 2010/0290988 A1 | 11/2010 | Cheeseman et al. | | |
| 2011/0189089 A1 | 8/2011 | Nairne et al. | | |
| 2012/0053337 A1 | 3/2012 | Li et al. | | |
| 2012/0108858 A1 | 5/2012 | Kiselev | | |
| 2012/0289716 A1 | 11/2012 | Suzuki et al. | | |
| 2012/0324715 A1 | 12/2012 | Kim | | |
| 2013/0001088 A1 | 1/2013 | Wang et al. | | |
| 2013/0274507 A1 | 10/2013 | Berg | | |
| 2013/0336890 A1 | 12/2013 | Thiele et al. | | |
| 2013/0343990 A1 | 12/2013 | Luthra et al. | | |

OTHER PUBLICATIONS

Zaragoza Dorwald, Side Reactions in Organic Synthesis, 2005, Wiley-VCH Verlag GmbH & Co. KGaA, Weinheim, Preface. p. IX.*
The International Search Report and Written Opinion dated Jun. 28, 2015 for International Application No. PCT/US2015/021215.
Bergman, J. et al. "Fluorine-18-Labeled Fluorine Gas for Synthesis of Tracer FMolecules" Nuclear Medicine & Biology, vol. 24, 1997, pp. 677-683, paragraph [7].
Jacobson, O. et al. "PET Designated Flouride-18 Production and Chemistry" Current Topics in Medicinal CHemistry, vol. 10, 2010, pp. 1048-1059; abstract, p. 1049, paragraph [1].
Alexoff, et al., Modular Automation in PET Tracer Manufacturing: Application of an Autosynthesizer to the Production of 2-Deoxy-2-[18F]Fluoro-d-Glucose, International Journal of Radiation Applications and Instrumentation. Part A, Applied Radiation and Isotopes, 1986, 37(10):1045-1061.

(Continued)

*Primary Examiner* — Paul A Zucker
(74) *Attorney, Agent, or Firm* — Quarles & Brady LLP (57) ABSTRACT

Methods, compositions, and systems related to preparing gaseous $^{18}$F-compounds for use in radiolabeling positron emission tomography (PET) tracer precursor compounds are disclosed. [$^{18}$F]fluoride ions produced by conventional methods are converted by reaction with an acid anhydride having the formula:

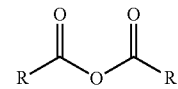

to a gaseous $^{18}$F-compound having the formula:

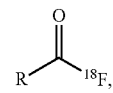

wherein each R is independently a substituted or unsubstituted, straight chain or branched $C_1$-$C_4$ alkyl group. The gaseous $^{18}$F-compounds, which also can be readily trapped on solid-phase extraction media or in organic solvents such as acetonitrile, provide an alternative source of [$^{18}$F]fluoride for use in the nucleophilic substitution reactions that are used to synthesize a large number of $^{18}$F-labeled PET imaging tracers, including 2-[$^{18}$F]fluoro-2-deoxyglucose (FDG).

30 Claims, 7 Drawing Sheets

(56) References Cited

OTHER PUBLICATIONS

De Kleijn, et al., Labelling with Reactor Produced 18F—III. Polymer Supported 18F as a Fluorinating Agent, International Journal of Applied Radiation and Isotopes, 1977, 28:591-594.
De Kleijn, et al., Labelling with Reactor-Produced Fluorine-18, Journal of Labelled Compounds and Radiopharmaceuticals, 1977, 13(2):212-213.
Schou, Synthesis and Evaluation of New NET Radioligands, published and printed by Karolinska Univerisyt Press, Sweden, Copyright Magnus Schou, 2006, ISBN 91-7140-773-1, 47 pages.

* cited by examiner

GASEOUS F-18 TECHNOLOGIES

CROSS-REFERENCES TO RELATED APPLICATIONS

This application is a 371 application of PCT/US2015/021215 filed Mar. 18, 2015 which is based on, claims the benefit of, and incorporates herein by reference U.S. Provisional Patent Application No. 61/954,839 filed Mar. 18, 2014.

STATEMENT REGARDING FEDERALLY SPONSORED RESEARCH

Not Applicable.

BACKGROUND OF THE INVENTION

1. Field of the Invention

The field of the invention is the manufacture of $^{18}$F-labeled radiopharmaceuticals and particularly, the production and use of anhydrous $^{18}$F-containing gases for more efficient and cost effective $^{18}$F-labeling compounds used in PET imaging.

2. Description of the Related Art

Compounds that are labeled with the radionuclide Fluorine-18 ($^{18}$F) are used as diagnostic imaging agents in positron emission tomography (PET). For example, 2-[$^{18}$F]fluoro-2-deoxy-D-glucose (FDG) is one tracer used in PET imaging. This molecule, labeled with $^{18}$F, behaves in a way similar to glucose in the first step of its destabilization in the human body and allows a user to map and quantify this fundamental mechanism. It is indicated for diagnosis of numerous diseases. FDG and its preparation are described in U.S. Pat. Nos. 4,617,386, 4,794,178, 5,169,942, 5,264,570, 5,436,325, 5,759,513, 5,808,020, 5,932,178, and 6,172,207.

FDG and many other $^{18}$F-labeled compounds are used in clinical PET imaging of human diseases. However, the radiochemical synthesis of such $^{18}$F-labeled compounds is often limited by the reactivity of the raw material [$^{18}$F]fluoride. Specifically, the difficulty in producing [$^{18}$F]fluoride in an anhydrous form has been a major obstacle to the efficient syntheses of many commonly used PET tracers from tracer precursor compounds.

Conventionally, PET precursor compounds are labeled with $^{18}$F using the [$^{18}$F]fluoride ions produced when the accelerated protons produced by a proton accelerator such as a cyclotron target the $^{18}$O atoms in $^{18}$O enriched water. The resulting [$^{18}$F]fluoride ions are dissolved in the water solution, and this water solution cannot be transported long distances without sustaining high losses within the transport tubing.

The current processing methods for preparing and using [$^{18}$F]fluoride for $^{18}$F-labeling of PET tracer precursor compounds are time-consuming, incur loss of radioactivity, and present inflexibility for design of new radiosynthesis paradigms, such as the "chemistry-on-a-chip" model. Furthermore, the conventional model for manufacturing and distributing $^{18}$F-labeled compounds, such as FDG, to hospitals for clinical PET imaging has been limited to a centralized distribution scheme whereby networks of PET tracer distributors ship FDG and other tracers to hospitals via trucks as a final product to be administered to patients.

A new "decentralized" distribution model has been proposed by others that entails distributing raw material [$^{18}$F]fluoride to various PET imaging sites, such as hospitals, wherein each site would have dedicated $^{18}$F radiochemistry equipment capable of converting the [$^{18}$F]fluoride to $^{18}$F-products according to a "dose-on-demand" model. This concept has not been put into practice because conventional radiochemistry methods do not efficiently convert [$^{18}$F]fluoride in water solution into useful $^{18}$F-products, such as PET tracer compounds.

Typically, [$^{18}$F]fluoride is produced in a cyclotron target containing $^{18}$O-enriched water, with enrichment of $^{18}$O exceeding 95%. In contrast, natural water contains only 0.2% enrichment of $^{18}$O. The enrichment process is costly, resulting in high cost for $^{18}$O enriched water and the desire to efficiently recycle the enriched water for reuse.

After the proton irradiation of the targeted $^{18}$O-enriched water is completed, the resulting [$^{18}$F]fluoride-containing water is forced by overpressure through Teflon or polypropylene tubing over long distances (20-60 feet) to radiochemistry hot cells, where further radiochemical processing is performed. Because water naturally adheres to the tubing, there are unavoidable losses of [$^{18}$F]fluoride associated with the transport process. In most facilities, a rinse of the target with either normal water (mainly $^{16}$O-water) or $^{18}$O-enriched water is performed to obtain a large portion of the adhered [$^{18}$F]fluoride, but this step has significant disadvantages related to the high cost of $^{18}$O-enriched water and the limited cost savings associated with recycling.

The radiochemistry process, which occurs in a separate radiochemistry hot cell, generally begins by separating the [$^{18}$F]fluoride from the $^{18}$O-enriched water, typically using an anion-exchange cartridge. [$^{18}$F]fluoride is trapped on the cartridge while the $^{18}$O-enriched water is collected, stored and returned to the vendor for recycling.

If the target rinse is performed with $^{18}$O-enriched water, then the $^{18}$O-enrichment of the water remains high, and the material is recycled with minimal cost. However, the cost of the $^{18}$O water rinse is substantial (typically more than $125). On the other hand, if normal water is used for the rinse, then the isotopic enrichment of the collected $^{18}$O water is compromised such that the collected water will have much less value when sold back to the vendor.

The existing methods for preparing and transporting [$^{18}$F]fluoride for labeling PET tracer precursor compounds present a number of significant challenges. As noted above, such methods result in significant loss of the [$^{18}$F]fluoride raw material in transfer lines. Furthermore, significant radioactive decay occurs in the time needed to dry down the $^{18}$F in the radiochemistry hot cell. In addition, because of the volume of the $^{18}$O-enriched water within which the [$^{18}$F]fluoride is delivered, current methods limit the potential designs that can be used for radiochemistry processing. For example, microfluidic processing cannot be done with such large volumes (typically greater than 2 mL), and such volumes necessitate using a non-microfluidic $^{18}$F dry-down apparatus and procedures. Similarly, transfer of [$^{18}$F]fluoride used in conventional methods to a microfluidic chip involves significant challenges and large loss of [$^{18}$F]fluoride. Finally, the existing $^{18}$F-labeling technologies often leave the [$^{18}$F]fluoride in the presence of trace metal ions that hinder its reactivity, thus further decreasing incorporation yields into $^{18}$F-labeled radiopharmaceuticals.

Thus, there is a need for improved methods for preparing, transporting, and incorporating $^{18}$F-labels into PET tracer precursor compounds to make PET tracer compounds for clinical use.

SUMMARY OF THE INVENTION

The present invention provides methods and systems for preparing gaseous $^{18}$F containing compounds for use in labeling PET precursor compounds with $^{18}$F, as well as related compositions and compounds.

In one exemplary embodiment, the invention entails the conversion of [$^{18}$F] fluoride produced by exposing $^{18}$O-enriched water to a cyclotron beam of accelerated protons into a gaseous chemical form (i.e., a gaseous $^{18}$F-compound) at close proximity to the cyclotron target. As a result of this conversion to a gaseous $^{18}$F-compound, the $^{18}$F-radioactivity can be effectively separated from the $^{18}$O-enriched water with minimal loss and then transported to radiochemical hot cells through gas lines, again with minimal transport losses. Using the disclosed method, the gaseous $^{18}$F-compounds can be produced from [$^{18}$F]fluoride with greater than 95% efficiency.

As a non-limiting example, $^{18}$F acetyl fluoride, an exemplary gaseous $^{18}$F-compound that can be produced using the disclosed method, has a boiling point of 21° C. It is therefore a gas at room temperature, and can be easily transported through polymer tubing without impediment or loss of the attached $^{18}$F. Furthermore, it is stable at room temperature, can be readily converted back to [$^{18}$F]fluoride in basic solutions, and can also be converted directly to $^{18}$F-labeled products by reaction with PET tracer precursors to produce the corresponding PET tracer.

After transport from the cyclotron, the gaseous $^{18}$F-compounds can be easily trapped in an organic solvent such as acetonitrile or on a solid-phase extraction cartridge as a first step in radiochemical processing. By inclusion of a phase-transfer catalyst in the trapping solution, the gaseous $^{18}$F-compounds can provide [$^{18}$F]fluoride reactants for the nucleophilic substitution reactions used to synthesize a large number of $^{18}$F-labeled radiopharmaceuticals, including 2-[$^{18}$F]fluoro-2-deoxyglucose (FDG), the most common PET imaging radiopharmaceutical. The disclosed methods can potentially replace more complicated, costly, and time-consuming transport and production methods associated with $^{18}$F-labeling of radiopharmaceuticals.

Accordingly, in a first aspect, the disclosure encompasses a method in preparing a gaseous $^{18}$F-compound for labeling a positron emission tomography (PET) tracer precursor compound with $^{18}$F. The method includes the steps of (1) contacting a composition comprising [$^{18}$F]fluoride ions with an anhydride having the formula:

wherein each R is independently a substituted or unsubstituted, straight chain or branched $C_1$-$C_4$ alkyl group. The two R groups may be the same, or they may be different. For example, the first R may be methyl and the second R may be tert-butyl. In the subsequent reaction, a gaseous $^{18}$F-compound is produced having the formula:

In some other embodiments, the disclosure encompasses a method for preparing a gaseous $^{18}$F-compound from [$^{18}$F]fluoride ions produced by a proton accelerator. The method includes the steps of (1) contacting a composition comprising the [$^{18}$F]fluoride ions with an acyl halide having the formula:

wherein X is I, Br, or Cl, and each R is independently a substituted or unsubstituted, straight chain or branched $C_1$-$C_4$ alkyl group. In the subsequent reaction, a gaseous $^{18}$F-compound is produced having the formula:

Preferably, the gaseous $^{18}$F-compound is anhydrous. In some embodiments, the step of contacting the composition comprising [$^{18}$F]fluoride ions with the anhydride or acyl halide occurs at a temperature of 50-70° Celsius.

In some embodiments, R is an alkyl group that is substituted with one or more halogen atoms, such as, without limitation, fluorine or chlorine. In certain of these embodiments, R can be —$CH_2F$, —$CH_2Cl$ or —$CHFCH_3$.

In some other embodiments, R is an unsubstituted alkyl group. In certain of these embodiments, R can be —$CH_3$, —$CH_2CH_3$, —$CH_2CH_2CH_3$, —$CH(CH_3)_2$, or —$C(CH_3)_3$.

In some embodiments, the composition comprising the [$^{18}$F]fluoride ions further includes an anion-exchange resin on which the [$^{18}$F]fluoride ions are trapped. Optionally, the composition comprising [$^{18}$F]fluoride ions trapped on the anion-exchange resin is produced by contacting the anion-exchange resin with a water solution comprising [$^{18}$F]fluoride ions and subsequently drying the resin by rinsing with acetone followed by a flow of nitrogen. In some embodiments, the anion exchange resin is a weakly basic, macroporous anion exchange resin having beads of uniform size, and may further comprise a styrene-divinylbenzene copolymer matrix and tertiary and quaternary ammonium groups. A preferred anion exchange resin is a LEWATIT® MP-64 carbonate form resin.

In certain embodiments, the water solution comprising [$^{18}$F]fluoride ions is produced by contacting one or more accelerated protons with $^{18}$O-enriched target water. In certain embodiments, the step of contacting one or more accelerated protons with the $^{18}$O-enriched target water is performed in close proximity to the step of contacting the composition comprising [$^{18}$F]fluoride ions trapped on the anion-exchange resin with the anhydride to produce the gaseous $^{18}$F-compound. In certain embodiments, the step of contacting one or more accelerated protons with the $^{18}$O-enriched target water is performed within 15 feet of the step of contacting the composition comprising [$^{18}$F]fluoride ions trapped on the anion-exchange resin with the anhydride to produce the gaseous $^{18}$F-compound.

In certain embodiments, the steps of contacting one or more accelerated protons with the $^{18}$O-enriched target water and contacting the composition comprising [$^{18}$F]fluoride ions trapped on the anion-exchange resin with the anhydride to produce the gaseous $^{18}$F-compound are both performed within a cyclotron vault. In certain such embodiments, the gaseous $^{18}$F-compound is stored within the cyclotron vault.

In some embodiments, the gaseous $^{18}$F-compound is stored in a microfluidic device. In some embodiments, the gaseous $^{18}$F-compound is transported to a radiochemistry hot cell, optionally via polymeric tubing.

In some embodiments, the method further includes the step of contacting the gaseous $^{18}$F-compound with a PET tracer precursor compound, whereby the PET tracer precursor compound is labeled with $^{18}$F to produce an $^{18}$F-labeled PET tracer compound. In some such embodiments, the $^{18}$F-labeled PET tracer compound produced is 2-[$^{18}$F] fluoro-2-deoxyglucose (FDG). In some such embodiments, the $^{18}$F-labeled PET tracer compound produced is [$^{18}$F] tetrafluoroborate (BF$_4^-$).

Some embodiments further include the step of contacting the gaseous $^{18}$F-compound with a composition comprising an organic solvent, whereby the gaseous $^{18}$F-compound is trapped within the composition. In some such embodiments, the organic solvent is acetonitrile. Optionally, the composition comprising the organic solvent further comprises a phase transfer catalyst, a PET tracer precursor compound, or both. Optionally, the phase transfer catalyst is tetraethylammonium bicarbonate.

In some embodiments, the method further includes the step of contacting the gaseous $^{18}$F-compound with a second gas to form an $^{18}$F-labeled radioactive product. Optionally, the second gas is BF$_3$, and the $^{18}$F-labeled radioactive product is [$^{18}$F]BF$_4^-$.

In a second aspect, the disclosure encompasses an $^{18}$F-compound having the formula:

wherein R is a substituted or unsubstituted, straight chain or branched C$_1$-C$_4$ alkyl group, with the proviso that R is not —CH$_3$.

In some embodiments, R is an alkyl group that is substituted with one or more halogen atoms, including without limitation fluorine or chlorine. In some such embodiments, R is —CH$_2$F, —CH$_2$Cl, or —CHFCH$_3$.

In some other embodiments, R is an unsubstituted alkyl group. In some such embodiments, R is —CH$_2$CH$_3$, —CH$_2$CH$_2$CH$_3$, —CH(CH$_3$)$_2$, or —C(CH$_3$)$_3$.

In a third aspect, the disclosure encompasses a composition for labeling a positron emission tomography (PET) tracer precursor compound with $^{18}$F. the composition includes (1) an $^{18}$F-compound having the formula:

wherein R is a substituted or unsubstituted, straight chain or branched C$_1$-C$_4$ alkyl group; and (2) an organic solvent.

In some embodiments, R is an alkyl group that is substituted with one or more halogen atoms, such as without limitation, chlorine or fluorine. In some embodiments, R is —CH$_2$F, —CH$_2$Cl, or —CHFCH$_3$.

In some other embodiments, R is an unsubstituted alkyl group. In such embodiments, R may optionally be —CH$_3$, —CH$_2$CH$_3$, —CH$_2$CH$_2$CH$_3$, —CH(CH$_3$)$_2$, or —C(CH$_3$)$_3$.

In some embodiments, the organic solvent is acetonitrile.

In some embodiments, the organic solvent is tetrahydrofuran.

In some embodiments, the organic solvent is an alcohol (methanol, ethanol, etc.), whereby the gaseous [$^{18}$F]fluoride immediately forms [$^{18}$F]HF.

In some embodiments, the composition further includes a phase-transfer catalyst. Optionally, the phase transfer catalyst is tetraethylammonium bicarbonate.

In some embodiments, the composition may further include a PET tracer precursor compound.

In some embodiments, the gaseous [$^{18}$F]fluoride is trapped on a solid-phase extraction cartridge. This can effectively concentrate the gaseous [$^{18}$F]fluoride for subsequent elution by an organic solvent in a small volume.

In some embodiments, the gaseous [$^{18}$F]fluoride is trapped on a solid-phase extraction cartridge for transport of the $^{18}$F-radioactivity to a distant site as a solid substance that can be easily shielded. At the distant site, the acyl [$^{18}$F] fluoride is eluted from the cartridge with an organic solvent.

In some embodiments, the solid-phase extraction medium for trapping gaseous [$^{18}$F]fluoride is Porapak N.

In some embodiments, the solid-phase extraction medium for trapping gaseous [$^{18}$F]fluoride is Porapak Q.

In some embodiments, the solid-phase extraction medium for trapping gaseous [$^{18}$F]fluoride is Oasis WAX.

In a fourth aspect, the disclosure encompasses a system for producing a gaseous $^{18}$F-compound for labeling a positron emission tomography (PET) tracer precursor compound with $^{18}$F. The system includes $^{18}$O-enriched target water; a proton accelerator configured to produce a beam of accelerated protons in contact with the target water at a target location; an anion-exchange resin in close proximity to the target location; a gaseous [$^{18}$F]fluoride production apparatus that includes the additional hardware needed to form the gaseous [$^{18}$F]fluoride; and a transport tube capable of transporting a gas produced on the surface of the ion exchange resin to another location.

In some embodiments, the target location and the ion exchange resin are less than 15 feet apart and the gaseous [$^{18}$F]fluoride production apparatus is adjacent to the ion exchange resin.

In some embodiments, the proton accelerator is a cyclotron at least partially surrounded by the walls of a cyclotron vault, and the target location, the ion exchange resin, and the first conduit are located inside of the walls of the cyclotron vault. In some such embodiments, the transport tube connects the gaseous $^{18}$Ffluoride production apparatus to a gas storage reservoir within the cyclotron vault.

In some embodiments, the transport tube is greater than twenty feet in length and extends to the outside of the cyclotron vault. In some such embodiments, the second conduit is capable of transporting the gas to a radiochemistry hot cell. In some such embodiments, the transport tube is greater than sixty feet in length.

In some embodiments, the system further includes an anhydride having the formula:

wherein each R is independently a substituted or unsubstituted, straight chain or branched C$_1$-C$_4$ alkyl group.

In some embodiments, the transport tube contains a gaseous $^{18}$F-compound having the formula:

wherein R is a substituted or unsubstituted, straight chain or branched $C_1$-$C_4$ alkyl group. In some such embodiments, R is an alkyl group that is substituted with one or more halogen atoms, such as without limitation chlorine or fluorine. In such embodiments, R is optionally —$CH_2F$, —$CH_2Cl$, or —$CHFCH_3$.

In other embodiments, R is an unsubstituted alkyl group. In some such embodiments, R is —$CH_3$, —$CH_2CH_3$, —$CH_2CH_2CH_3$, —$CH(CH_3)_2$, or —$C(CH_3)_3$.

In a fifth aspect, the disclosure encompasses a system for producing a gaseous $^{18}F$-compound for labeling a positron emission tomography (PET) tracer precursor compound with $^{18}F$. The system includes a reagent delivery valve in communication with a source of $^{18}F$-fluoride and at least one precursor for reacting with the $^{18}F$-fluoride to provide a gaseous $^{18}F$-compound; a first bank including a first set of columns, a selected one of the first set of columns reversibly coupled to the reagent delivery valve; a second bank including a second set of columns, a selected one of the second set of columns reversibly coupled to the selected one of the first set of columns; and an output selector valve reversibly coupled to the selected one of the second set of columns for recovery of the gaseous $^{18}F$-compound. Each of the first bank and the second bank are independently rotatable about an axis to couple any one of the first set of columns in the first bank with any one of the second set of columns in the second bank, and when each of the reagent delivery valve, the first bank, the second bank, and the output selector valve are coupled, a continuous fluid pathway is formed between the reagent delivery valve and the output selector valve.

In some embodiments, the first set of columns are trap columns for trapping the $^{18}F$-fluoride.

In some embodiments, the second set of columns are purifications columns for purifying the gaseous $^{18}F$-compound.

These and other features, aspects, and advantages of the present invention will become better understood upon consideration of the following detailed description, drawings, and appended claims.

DETAILED DESCRIPTION OF THE INVENTION

In one exemplary embodiment, the disclosure encompasses a highly efficient method to transport $^{18}F$ isotope produced via the $^{18}O(p,n)^{18}F$ reaction facilitated by a proton accelerator such as a cyclotron. In addition to reducing the $^{18}F$ loss associated with conventional transport using [$^{18}F$]fluoride, the method results in greater efficiency of usage of the raw material $^{18}O$-enriched water used to produce the $^{18}F$ isotope.

Typically, [$^{18}F$]fluoride is produced in a cyclotron target containing $^{18}O$-enriched water with enrichment of $^{18}O$ exceeding 95%. Natural water contains only 0.2% enrichment of $^{18}O$. The enrichment process is costly, resulting in high cost of $^{18}O$-enriched water, and the desire to reuse (recycle) the material. After the proton irradiation is completed, the $^{18}F$-containing water is forced by overpressure through Teflon or polypropylene tubing a long distance (20-60 feet) to radiochemistry hot cells where further radiochemical processing is performed.

Since water naturally adheres to the tubing, there are unavoidable losses of $^{18}F$ associated with the transport process. In most facilities, a rinse of the target with either normal water (mainly $^{16}O$-water) or $^{18}O$-enriched water is performed to obtain a large portion of the adhered $^{18}F$-radioactivity, but this step has significant disadvantages related to the high cost of $^{18}O$-enriched water and the cost savings associated with recycling.

The radiochemistry process starts with a process of separating the [$^{18}F$]fluoride from the $^{18}O$-enriched water, typically using an anion-exchange cartridge. [$^{18}F$]fluoride is trapped on the cartridge while the $^{18}O$-enriched water is collected, stored and sold back to the vendor for recycling. If the target rinse is performed with $^{18}O$-enriched water, then the $^{18}O$-enrichment of the water remains high, and the material remains useful for recycling. However, the cost of the $^{18}O$ water rinse is substantial (typically >$125). On the other hand, if normal water is used for the rinse, then the isotopic enrichment of the collected $^{18}O$ water is compromised such that the collected water will have much less value to be sold back to the vendor for recycling.

In an exemplary embodiment, the invention entails the conversion of [$^{18}F$]fluoride to a gaseous chemical form (a gaseous $^{18}F$-compound) at close proximity to the cyclotron target so that the $^{18}F$-radioactivity can be effectively separated from the $^{18}O$-enriched water with minimal losses and then transported to radiochemical hot cells through gas lines, again with minimal transport losses.

Figure 1A:
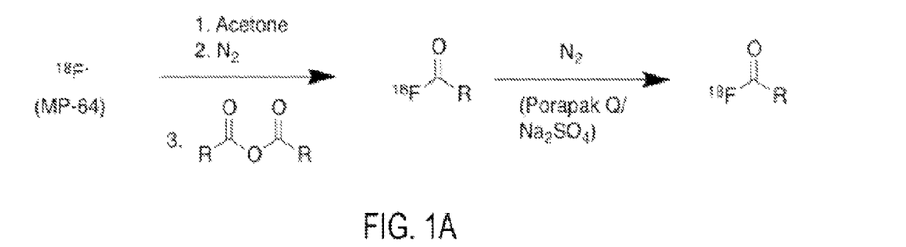
FIG. 1A is generic reaction scheme for the production of the disclosed gaseous $^{18}F$-compounds using acid anhydrides.

Referring first to FIG. 1A, the gaseous $^{18}F$-compound is produced by contacting a composition containing the [$^{18}F$] fluoride with an anhydride having the formula shown below the leftmost arrow. Each R is independently a substituted or unsubstituted, straight chain or branched $C_1$-$C_4$ alkyl group, and the R groups may be the same or different. The resulting reaction produces the gaseous $^{18}F$-compound having the formula shown in the center. Optionally, the composition is first dried by acetone and nitrogen, and the gaseous $^{18}F$-compound may be trapped in a solid phase extraction medium, such as Porapak Q, as illustrated by the rightmost arrow.

Figure 1B:
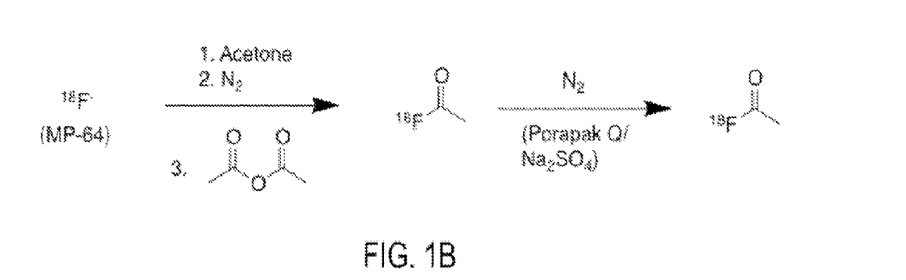
FIG. 1B is a specific reaction scheme for the production of $^{18}F$ acetyl fluoride from [$^{18}F$]fluoride ion using acetic anhydride.

One specific exemplary gaseous $^{18}F$-compound produced by the method is $^{18}F$-labeled acetyl fluoride ([$^{18}F$]AcF), although the invention is not limited to use of this chemical form. The production of [$^{18}F$]AcF using acetic anhydride is illustrated in FIG. 1B with R=$CH_3$. Gaseous [$^{18}F$]AcF is produced from [$^{18}F$]fluoride in greater than 95% efficiency using the disclosed process. Acetyl fluoride has a boiling point of 21° C. It is therefore a gas at room temperature, and easily transported through polymer tubing.

Figure 1C:
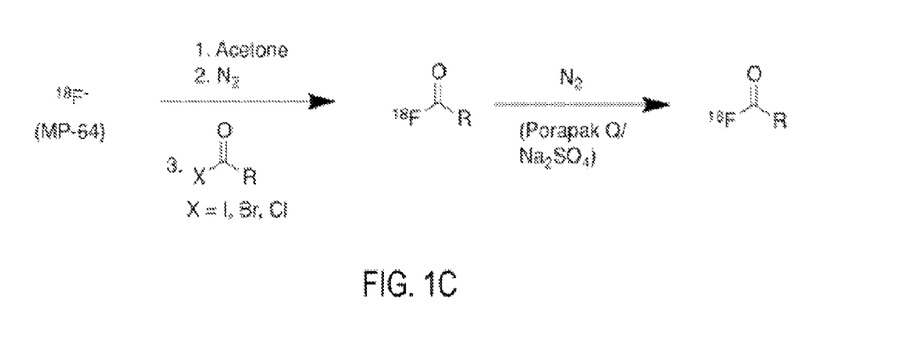
FIG. 1C is generic reaction scheme for the production of the disclosed gaseous $^{18}F$-compounds using acid halides.

Referring now to FIG. 1C, the gaseous $^{18}F$-compound can alternatively be produced by contacting a composition containing the [$^{18}F$]fluoride with an acid halide having the formula shown below the leftmost arrow. Each R is independently a substituted or unsubstituted, straight chain or branched $C_1$-$C_4$ alkyl group, and the R groups may be the same or different. The resulting reaction produces the gaseous $^{18}F$-compound having the formula shown in the center. Optionally, the composition is first dried by acetone and nitrogen, and the gaseous $^{18}F$-compound may be trapped in a solid phase extraction medium, such as Porapak Q, as illustrated by the rightmost arrow.

After transport from the cyclotron, [$^{18}F$]AcF is easily trapped in an organic solvent such as acetonitrile as a first step in radiochemical processing. By including a phase-transfer catalyst in the trapping solution, [$^{18}F$]AcF provides [$^{18}F$]fluoride for nucleophilic substitution reactions for synthesis of a large number of $^{18}F$-labeled radiopharmaceuticals, including 2-[$^{18}F$]fluoro-2-deoxyglucose (FDG), the most common PET imaging radiopharmaceutical.

Figure 2:
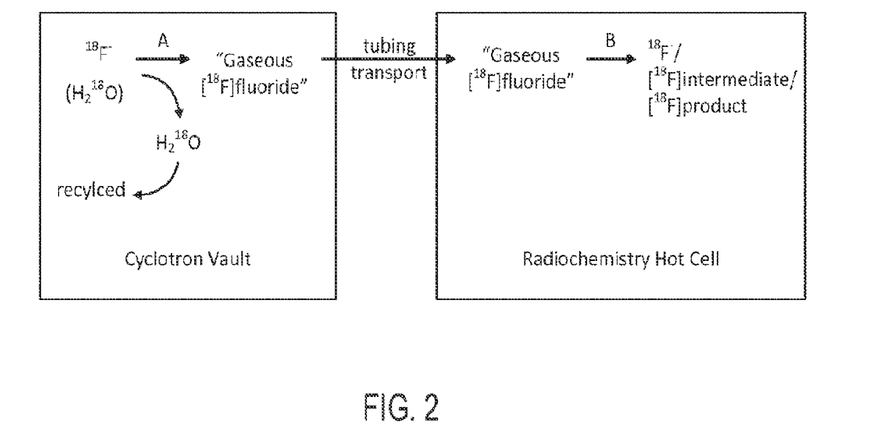
FIG. 2 is a schematic drawing of an exemplary production, transport, and use system for the disclosed gaseous $^{18}F$-compounds.

Referring now to FIG. 2, in an exemplary embodiment of the disclosed method, the [$^{18}F$]fluoride is first converted to a gaseous $^{18}F$-compound, such as [$^{18}F$]AcF (FIG. 2, A), with efficient collection of $^{18}O$-enriched water for recycling (FIG. 2, left box). The target may be rinsed with normal water, but since there is minimal tubing volume between the target and the conversion module, the target and lines can be quickly dried to avoid loss of enrichment of the collected $^{18}O$-enriched water.

In a second optional step, the gaseous $^{18}F$-compound can be stored in a vessel within the vault for distribution to multiple processes.

In a third step, the gaseous $^{18}F$-compound, such as [$^{18}F$]AcF, is transported through polymer tubing to the radiochemistry hot cell (FIG. 2, center). The transport process may be driven by an inert sweep gas such as nitrogen. Losses of gaseous radioactivity in the polymer tubing are minimal.

In a fourth step, the gaseous $^{18}F$-compound, such as [$^{18}F$]AcF, is trapped in an organic solvent and subsequently reacted with a substrate containing a reactive leaving group to form a new C-$^{18}F$ bond, resulting in a new $^{18}F$-labeled compound (FIG. 2, B). A phase-transfer catalyst, such as tetraethylammonium bicarbonate, can help facilitate this reaction.

Alternatively, the gaseous $^{18}F$-compound could be reacted with another gas in the gas phase to form new radioactive products. In a non-limiting example, [$^{18}F$]AcF is reacted with $BF_3$ to form acetyl [$^{18}F$]$BF_4^-$.

The gaseous $^{18}F$-compound can be trapped within a microfluidic device to allow $^{18}F$ radiochemistry to be done within small processing volumes. Further reaction of the $^{18}F$ and radiochemical processing would proceed according to known conventional methods.

Figure 3:
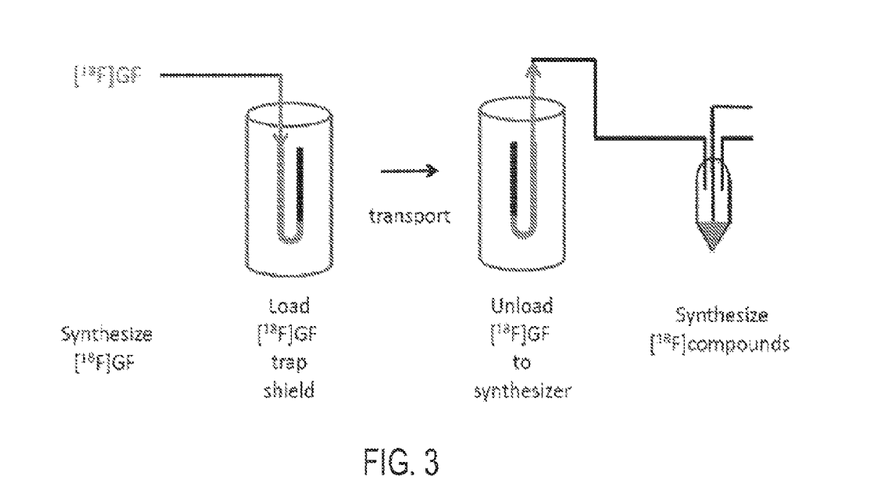
FIG. 3 is a schematic drawing of an exemplary production, transport, and use system for the disclosed gaseous $^{18}F$-compounds, illustrating the transportability of the $^{18}F$-compounds.

As illustrated in FIG. 3, in an alternative embodiment, the gaseous $^{18}F$-compound is loaded onto a [$^{18}F$]GF trap, which can then be shielded and safely transported and subsequently unloaded to the synthesizer.

The disclosed method presents a number of advantages over using conventional $^{18}F$ processing methods. First, because of the drastically decreased transport losses between the production site (the cyclotron target) and the radiochemistry reactor (the radiochemistry hot cell), the disclosed method results in more efficient use of the [$^{18}F$]fluoride produced in the cyclotron target and facilitates longer transport distances of $^{18}F$ to the radiochemistry hot cell. Typically, [$^{18}F$]fluoride in water cannot be delivered more than 60 feet in tubing without incurring significant losses. $^{18}F$ losses are directly proportional to transport tubing length, and can be as high as 30% when using conventional [$^{18}F$] fluoride solutions. The use of gaseous $^{18}F$-compounds instead of conventional [$^{18}F$]fluoride solutions to transport the $^{18}F$ virtually eliminates such losses.

Second, the disclosed method facilitates the highly efficient use of costly $^{18}O$-enriched water. Because the gaseous $^{18}F$-compound is produced in close proximity to the cyclotron target, and because the aqueous [$^{18}F$]fluoride solution containing the $^{18}O$-enriched water need not be transported long distances to the radiochemistry hot cell, successful recycling of the $^{18}O$-enriched water is easier and more cost-effective.

Third, the gaseous $^{18}F$-compounds produced by the method exhibit increased $^{18}F$ reactivity. The anhydrous nature of the gaseous $^{18}F$-compounds enhances the nucleophilicity of the attached [$^{18}F$]fluoride, making the compounds highly reactive radiofluorination agents. Accordingly, the gaseous $^{18}F$-compounds facilitate increased radiofluorination yields. Improvement in yields make practical the synthesis of certain compounds that have very poor yields using conventional methods, thus providing facile access to certain $^{18}F$-labeled radiopharmaceuticals that may be difficult to make using conventional aqueous [$^{18}F$]fluoride.

Furthermore, because of ease of synthesis when using the gaseous $^{18}F$-compound s, the disclosed method provides access to new radiochemistry platforms and compounds. For example, the tracer-on-demand approach, which requires a source of $^{18}F$ and utilizes chemistry-on-a-chip technology, has been in development for over ten years, but has not reached its full potential, because of the technological difficulties involved in concentrating and drying [$^{18}F$]fluoride in water. The disclosed gaseous [$^{18}F$]fluoride technology can provide reactive $^{18}$F for such fluorination platforms. Specifically, the disclosed gaseous $^{18}$F-compounds may be trapped under low temperature in a very small volume on a microfluidics chip. The subsequent steps of synthesizing FDG and other $^{18}$F-compounds on a microfluidics chip have already been developed and demonstrated, and are well-known in the art.

Fourth, the disclosed method simplifies the radiochemistry process by eliminating the $^{18}$F "dry-down" step in the radiochemical synthesis. The typical "dry-down" step, which is performed within the radiochemical module, is necessary when using conventional radiofluorination, because the [$^{18}$F]fluoride source material is provided in a water solution. However, the dry-down step requires time and incurs further $^{18}$F losses in a dry-down reactor or microfluidic [$^{18}$F]fluoride concentrator. In the disclosed method, the $^{18}$F is converted to an anhydrous gaseous form in close proximity to the proton accelerator, and the $^{18}$F is provided to the radiochemical module in this form. This eliminates the need for the dry-down step.

Fifth, the faster $^{18}$F transport and radiochemical processing facilitated by the disclosed method, together the increased reactivity of the fluorinating agent, will result in higher overall production yields of $^{18}$F radiopharmaceuticals.

Sixth, the disclosed method will facilitate the conversion of gaseous fluoride to other gaseous products, or reaction in the gas phase to form nongaseous $^{18}$F-products. The reactivity of the $^{18}$F gaseous fluoride compound will allow gas phase reactions with reactive substrates (e.g. BF$_3$).

Figure 4:
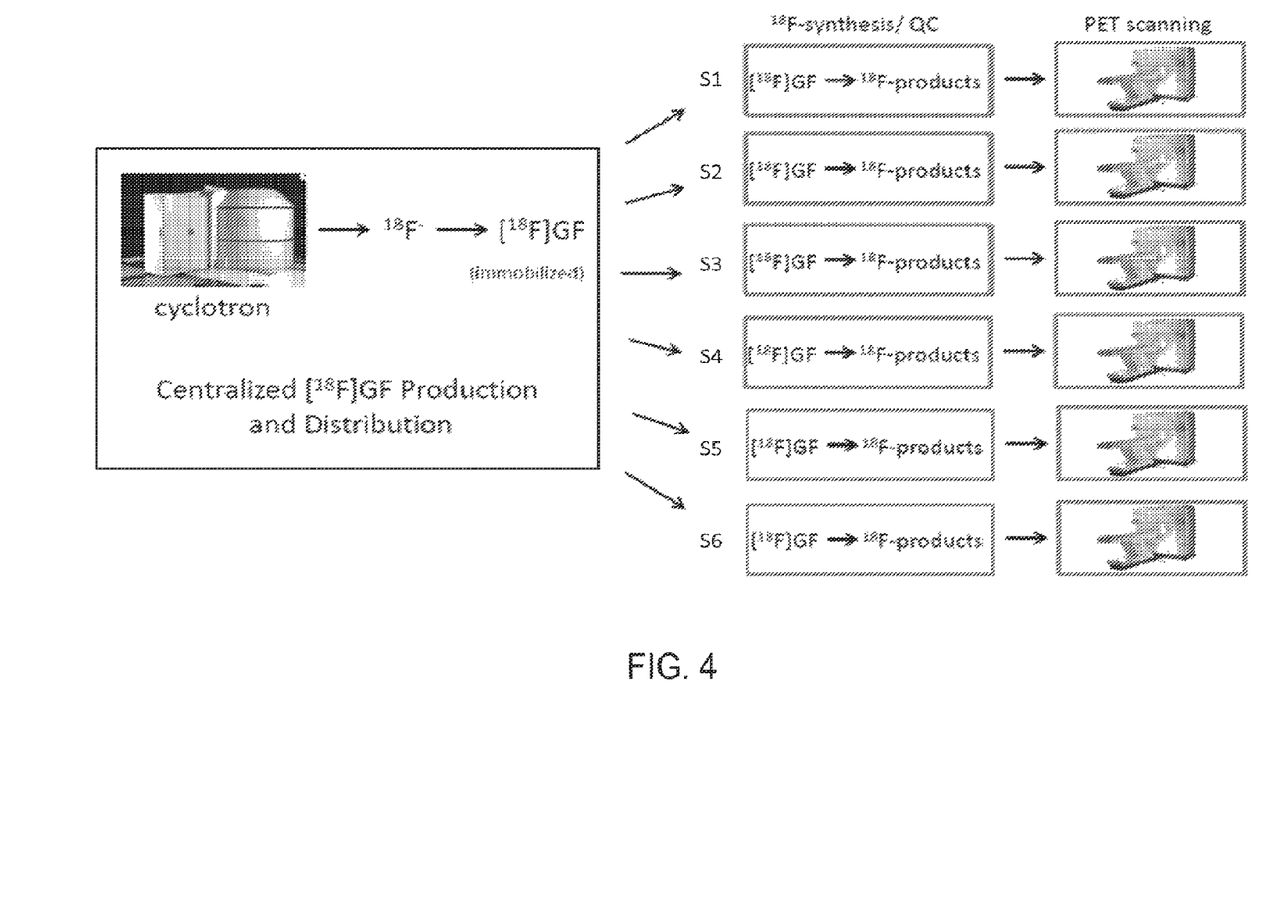
FIG. 4 is a schematic drawing of an exemplary centralized production and decentralized use system for the disclosed gaseous $^{18}F$-compounds, illustrating the use of gaseous [$^{18}F$]fluoride in a decentralized PET radiochemistry paradigm.

Seventh, the ease of trapping and storing the gaseous $^{18}$F-compounds of the disclosed method enables practical storage and use-on-demand, eliminating the need to run the cyclotron to make $^{18}$F isotope for each synthesis. Using the disclosed method, a large batch of gaseous $^{18}$F can be synthesized, stored in a shielded container in the cyclotron vault, and then partitioned out as needed to a number of radiochemistry processes throughout the day. In one exemplary centralized production and decentralized use system, centrally produced gaseous [$^{18}$F]fluoride can be distributed to multiple decentralized PET radiochemistry locations for making PET tracers for use as needed (see FIG. 4).

Gas lines can be easily piped to each radiochemistry hot cell and a simple shut-off valve used to control the amount of gaseous delivered to the hot cell. After the desired amount is obtained by trapping in a solution located in a dose calibrator, if necessary, the remainder in the line can be pushed back into the reservoir within the cyclotron vault. As an alternative, the disclosed gaseous $^{18}$F-compounds can be readily trapped within a microfluidic device.

Finally, the disclosed method will result in lower maintenance costs for $^{18}$F delivery lines and valves. Typically, the $^{18}$F water delivery lines must be replaced every three to six months, depending on usage levels. Because the radioactivity concentration of the disclosed gaseous $^{18}$F-compounds would be much less than for conventional aqueous [$^{18}$F] fluoride deliveries, the polymer delivery lines will incur much less radiation damage over the same period of time. Alternative materials for the transfer lines can be considered for the gaseous $^{18}$F-compounds such as stainless steel, since [$^{18}$F]fluoride adherence to these materials is no longer a consideration. Furthermore, the target water, which is included in conventional aqueous [$^{18}$F]fluoride deliveries, contains trace metals from the target that eventually can build up in the delivery lines and cause problems in valves. In contrast, the disclosed anhydrous gaseous $^{18}$F-compounds do not contain such trace metals.

EXAMPLES

Example 1: Production and Use of Gaseous $^{18}$F Acetyl Fluoride

Materials, Methods, and Results.

$^{18}$O-enriched target water was exposed to a beam of accelerated protons produced by a cyclotron. The resulting [$^{18}$F]fluoride solution was passed through an anion-exchange column (using 100 mg LEWATIT® MP-64 carbonate form ion-exchange resin) held at a temperature of 60° C. The [$^{18}$F]fluoride trapping efficiency of this anion-exchange resin was determined to be greater than 98%.

After passing through the anion-exchange column, the $^{18}$O-enriched water was collected for recycling. The target was rinsed with deionized water, and the rinse water was also passed through the anion-exchange column, but was not collected with the $^{18}$O-enriched water. The target and the lines leading to the anion-exchange column were subsequently dried under helium.

The anion-exchange resin was then rinsed with 10 mL acetone, and subsequently dried under nitrogen for 90 s. The anion-exchange resin was then wetted with acetic anhydride (0.25 mL) and allowed to react for 3 minutes at 60° C. to form acetyl [$^{18}$F]fluoride ([$^{18}$F]AcF).

Nitrogen was then swept through the anion-exchange column to carry the [$^{18}$F]AcF through a purification cartridge containing 1 g Porapak Q and 1 g anhydrous sodium sulfate. After passing through the purification cartridge, the [$^{18}$F]AcF is swept under nitrogen through polymeric tubing to the radiochemistry hot cell. The [$^{18}$F]AcF was trapped by bubbling it through a solution of acetonitrile at 0-20° C., or trapped on a Porapak N (100 mg) cartridge. Typical yields of [$^{18}$F]AcF were 85%, uncorrected for radioactive decay. Optionally, the acetonitrile solution contains a phase-transfer catalyst, such as tetraethylammonium bicarbonate, and/or a radiolabeling precursor.

Example 2: Production and Use of Other Gaseous $^{18}$F Fluoride Compounds

In this example, we report the production of other $^{18}$F gaseous fluoride compounds, including propanoyl [$^{18}$F]fluoride, butanoyl [$^{18}$F]fluoride, isobutanoyl [$^{18}$F]fluoride, 2-[$^{19}$F]fluoroacetyl [$^{18}$F]fluoride, 2-[$^{19}$F]fluoropropanoyl [$^{18}$F]fluoride, and chloroacetyl [$^{18}$F]fluoride. The results are compared with those reported above for the production of [$^{18}$F]AcF. For example, propanoyl [$^{18}$F]fluoride was prepared by the method described in Example 1, however, propionic anhydride (0.25 mL) was added to the MP-64 resin after trapping of [$^{18}$F]fluoride and drying with acetone and nitrogen.

Example 3: Trapping of Gaseous Acetyl [$^{18}$F]Fluoride on Porapak N Cartridge

After production and purification of [$^{18}$F]AcF as described in Example 1, it is swept under nitrogen to a cartridge containing 150 mg Porapak N resin, thereby trapping the [$^{18}$F]AcF with >98% efficiency. The [$^{18}$F]AcF is subsequently eluted from the Porapak N cartridge with an organic solvent, such as tetrahydrofuran or acetonitrile.

Example 4: Trapping of Gaseous $^{18}$F Acetyl Fluoride on Oasis WAX Cartridge

After production and purification of [$^{18}$F]AcF as described in Example 1, it is swept under nitrogen to a cartridge containing 100 mg Oasis WAX resin, thereby trapping the [$^{18}$F]AcF with >98% efficiency. The [$^{18}$F]AcF is subsequently eluted from the Porapak N cartridge with an organic solvent, such as tetrahydrofuran or acetonitrile.

Example 5: Trapping of Gaseous Acetyl [$^{18}$F]Fluoride in Stainless Steel or Polypropylene (PP) Tubing at Low Temperature After production and purification of acetyl [$^{18}$F]fluoride as described in Example 1, it was swept under nitrogen through a 40 cm loop of stainless steel tubing or polypropylene (PP) tubing (⅛ inch OD, 1/16 inch ID) in a liquid nitrogen-ethanol bath (−116° C.) thereby trapping the acetyl [$^{18}$F]fluoride within the tubing with >98% efficiency.

Example 6: Trapping of Gaseous Propanoyl [$^{18}$F]Fluoride in Stainless Steel or Polypropylene (PP) Tubing at Low Temperature After production and purification of propanoyl [$^{18}$F]fluoride as described in Example 2, it was swept under nitrogen through 40 cm stainless steel tubing or polypropylene (PP) tubing (⅛ inch OD, 1116 inch ID) in a dry ice-acetone bath (−78° C.) thereby trapping the propanoyl [$^{18}$F]fluoride within the tubing with >98% efficiency.

Example 7: Acyl [$^{18}$F]Fluorides as Novel Synthons for Radiofluorination

This example provides additional data obtained using the general methods outlined previously.

Objectives.

Current methods for delivery, extraction, and reformulation of [$^{18}$F]fluoride from proton-irradiated $^{18}$O-enriched water are far from ideal. We have developed gaseous acyl [$^{18}$F]fluorides as novel synthons that offer the ability to transfer [$^{18}$F]fluoride through gas lines in an anhydrous form.

Methods.

[$^{18}$F]fluoride in $^{18}$O-enriched water was trapped on an anion-exchange cartridge (MP-64, 40 mg) maintained at 70° C. The cartridge was rinsed with acetone and dried under nitrogen. Acetic or propionic anhydride were added to the cartridge and allowed to react for 3 min, producing acetyl [$^{18}$F]fluoride (AcF, Bp=21° C.) or propanoyl [$^{18}$F]fluoride (PrF, Bp=43° C.), respectively. The gaseous acyl [$^{18}$F] fluorides were swept by nitrogen from the MP-64 cartridge through an empty cartridge and two cartridges filled with Porapak-Q medium (900 mg each) maintained at 30-40° C. The product was then transported through polypropylene (PP) tubing to a distant radiochemistry location. The acyl [$^{18}$F]fluorides were efficiently trapped in acetonitrile and other polar organic solvents for subsequent radiofluorinations.

Results.

The unoptimized yields of purified acyl [$^{18}$F]fluorides were 60-75% uncorrected. Radiochemical purity was confirmed as >99% by GC-FID which is sensitive to radioactivity. Chemical purity was also >99% as shown by GC-FID. [$^{18}$F]AcF was transported through 15 m of PP tubing (0.79 mm ID) with <0.9% adsorbance to the tubing. Adsorbance of [$^{18}$F]PrF to PP tubing was significantly higher (3.8% over 15 m). $^{18}$F-fluorination of the mannose triflate FDG precursor in acetonitrile at 80° C. was >90% after addition of 10 mg tetraethylammonium bicarbonate to release the [$^{18}$F] fluoride into solution.

Conclusions.

$^{18}$F-labeled acyl fluorides were efficiently produced by a method that lends itself to automation. The anhydrous nature of acyl [$^{18}$F]fluorides may be advantageous for water-sensitive reactions. Furthermore, their gaseous form may inspire new paradigms for distribution and utilization of [$^{18}$F]fluoride.

Example 8: Automated Production of $^{18}$F-Labeled Acyl Fluorides as $^{18}$F-Fluorination Synthons Presence of trace water and metal impurities in preparations of $^{18}$F-fluoride can compromise radiofluorination efficiencies. Gaseous $^{18}$F-acyl fluorides represent a source of anhydrous, reactive $^{18}$F-fluoride. Accordingly, a system for high-yield, automated production of $^{18}$F-acetyl fluoride ($^{18}$F—AcF) or $^{18}$F-propanoyl fluoride ($^{18}$F—PrF) was developed.

With reference to FIGS. 5-11, an automated module 20 was developed to produce gaseous $^{18}$F-acyl fluorides via the reaction of $^{18}$F-fluoride with acetic anhydride or propanoyl anhydride for production of $^{18}$F—AcF or $^{18}$F—PrF, respectively. The module 20 includes two sets of disposable columns arranged radially about an axis of rotation of a cylindrical barrel or bank. A first bank 22 having an axis of rotation $A_1$ includes columns 24. In one example the columns 24 are MP-64 columns (130-140 mg) for trapping of $^{18}$F-fluoride with recovery of $^{18}$O-water and reaction to produce $^{18}$F-acyl fluorides. A second bank 26 includes columns 28. In one example, columns 28 are purification columns of Porapak Q (1 g) and sodium sulfate (1 g). The bank 22 and the bank 26 have a cylindrical "gun revolver" geometry that provides for at least about 12 runs from a single setup of the module 20 depending on the number of columns 24 and columns 28 included in each of the bank 22 and the bank 26. Multiple output lines including output line 30 are accommodated.

Figure 5A:
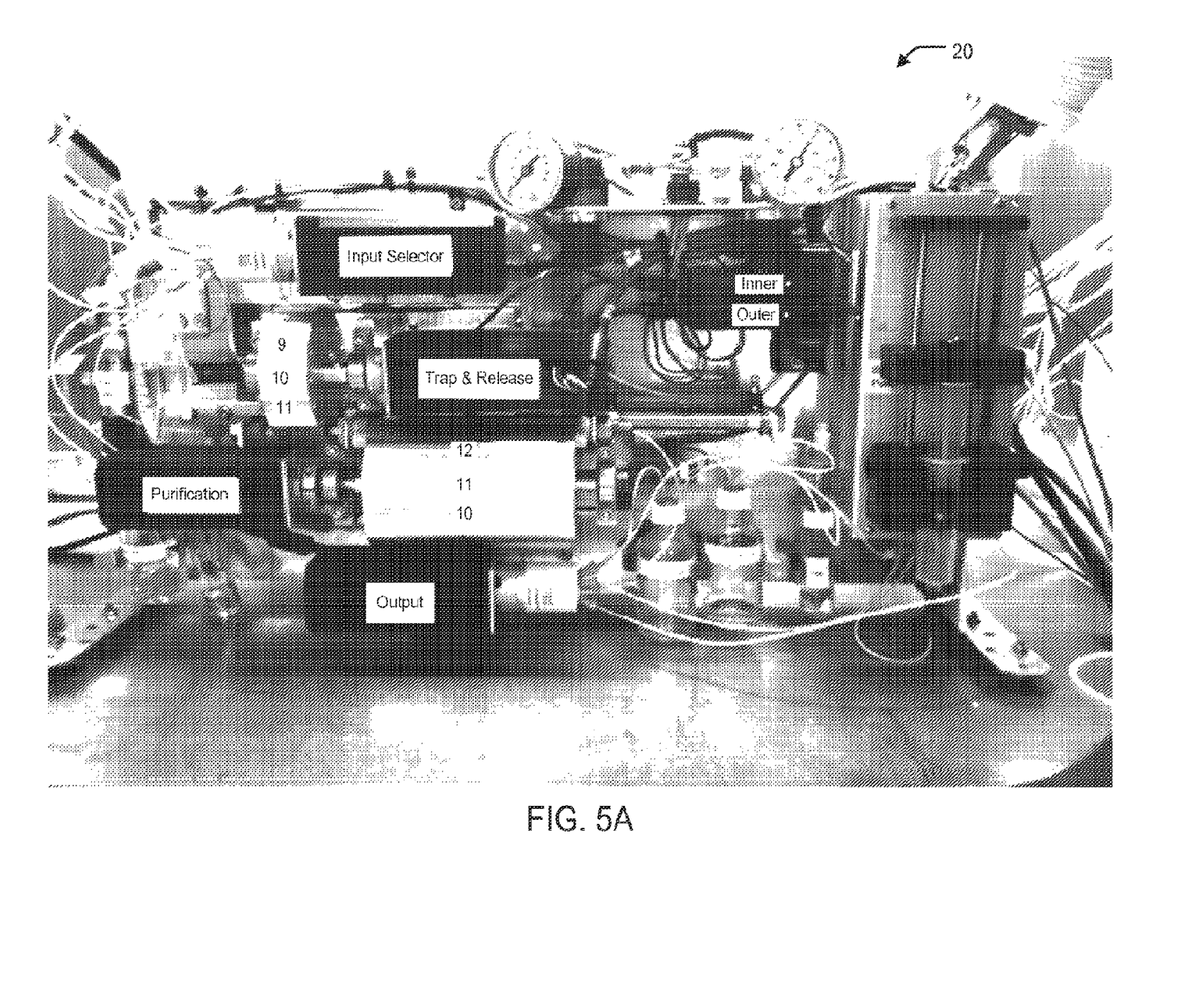
FIG. 5A is an image of an example system for producing gaseous $^{18}F$-compounds according the present disclosure.
Figure 5B:
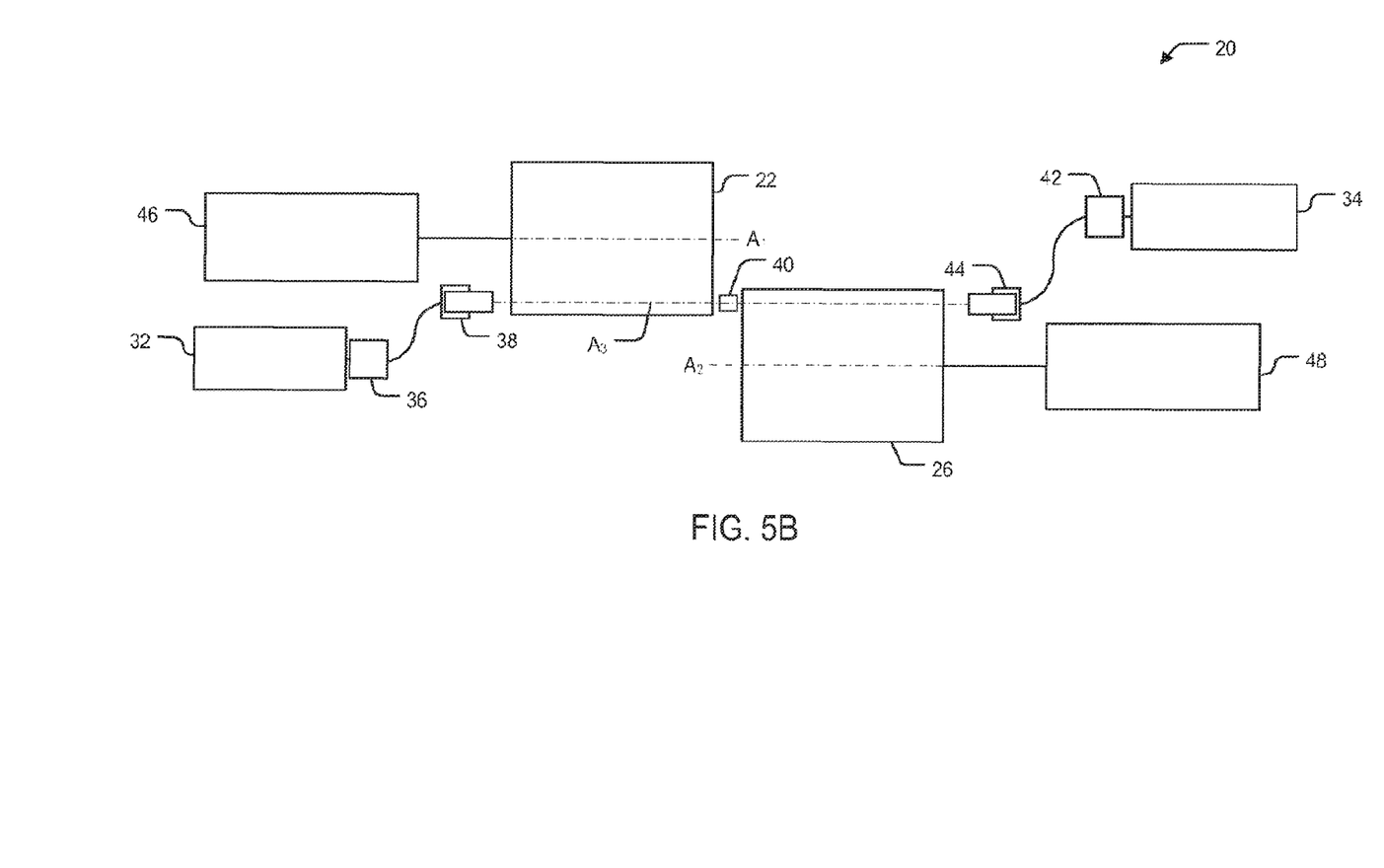
FIG. 5B is a schematic illustration of the example system of FIG. 5A.

The module 20 further includes a fluid flow path extending at least between a reagent delivery unit 32 and an output collection unit 34. The reagent delivery unit 32 includes a reagent delivery valve 36 that can be placed in fluid communication with the first bank 22 via a fitting 38 intermediate the valve 34 and the first bank 22. The first bank 22 can be placed in fluid communication with the second bank 26 via an intermediate fitting 40. Further, the second bank 26 can be placed in fluid communication with the output collection unit 34 via a fitting 44 and an output selector valve 42. When the components of the module 20 are fully coupled together (see FIG. 11A), a continuous fluid path extends from the reagent delivery unit 32 including the reagent delivery valve 36, through the fitting 38, a selected one of the columns 24 in the first bank 22, the intermediate fitting 40, a selected one of the columns 28 in the second bank 26, the fitting 44, and the output selector valve 42 of the output collection unit 34. However, when the components of the module 20 are separated (i.e., not in fluid communication; see FIG. 11B), each of the first bank 22 and the second bank 26 may be independently rotated about the corresponding axis of rotation to align a selected one of the columns 24 of the first bank 22 with a selected one of the columns 28 of the second bank 24 along the axis $A_3$. The first bank 22 is rotatable along the axis $A_1$ with a rotary unit 46. The second bank 26 is rotatable along the axis $A_2$ with a rotary unit 48. In one example, the rotary unit 46 and the rotary unit 48 may be electric motors.

Figure 6:
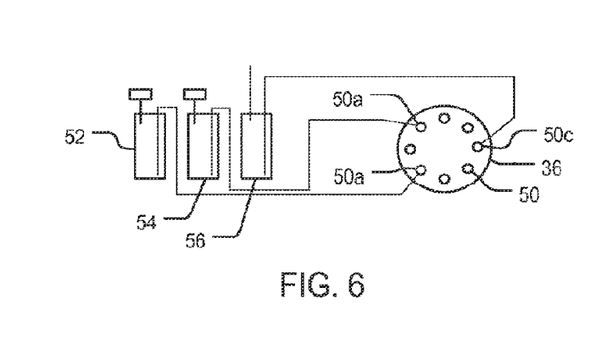
FIG. 6 is a schematic illustration a reagent delivery valve of the system of FIG. 5B.

Turning to FIG. 6, the reagent delivery valve 36 can be a selector valve operable to select between two or more sources. For example, the reagent delivery valve 36 can include a number of independently selectable ports 50. In one example, a first port 50a can be in fluid communication with a source 52 of a first precursor chemical (e.g., acetic anhydride), a second port 50b can be in fluid communication with a source 54 of a second precursor chemical (e.g., propanoyl anhydride or $^{18}$F-Fluoride), and a third port 50c can be in fluid communication with a source of a wash chemical (e.g., acetone). The reagent delivery valve 36 can further be in communication with a source of an inert gas (e.g., N$_2$), include a pressure monitor, or a combination thereof.

Figure 7:
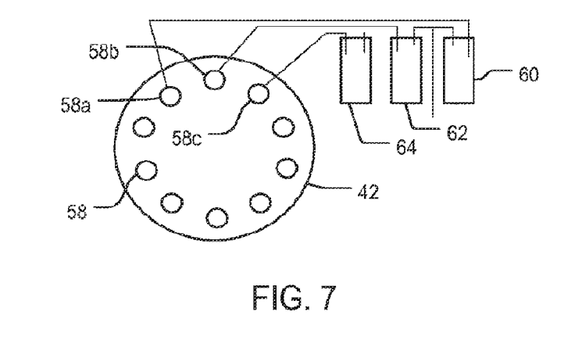
FIG. 7 is a schematic illustration an output selector valve of the system of FIG. 5B.

With reference to FIG. 7, the output selector valve 42 can be a selector valve operable to select between two or more sources. For example, the output selector valve 42 can include a number of independently selectable ports 58. In one example, a first port 58a can be in fluid communication with a waste collection tank 60 for recovery of a first material (e.g., $^{18}$O water), a second port 58b can be in fluid communication with a collection tank 62 for recovery of a second material (e.g., $^{16}$O waste water), and a third port 58c can be in fluid communication with a collection tank 64 for recovery of a waste stream. The output selector valve 36 can further be in communication with a collection tank or another vessel, analytical unit, or instrument for collection or use of a product stream.

Figure 8:
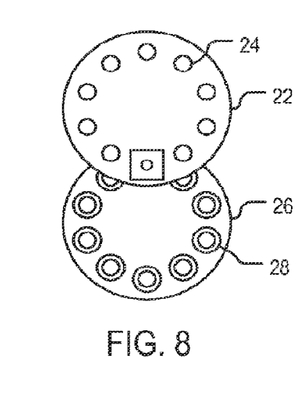
FIG. 8 is a schematic illustration showing a profile view along an axis of rotation of a first bank of columns and a second bank of columns of the system of FIG. 5B.
Figure 9:
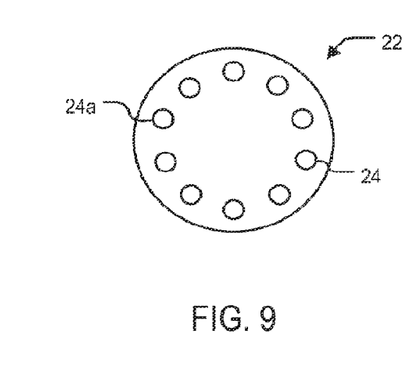
FIG. 9 is a schematic illustration of the first bank of columns of FIG. 8 in isolation.
Figure 10:
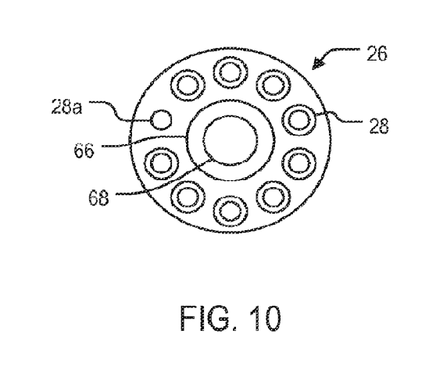
FIG. 10 is a schematic illustration of the second bank of columns of FIG. 8 in isolation.

FIGS. 8-10 show that the first bank 22 can include a number of radially arranged columns 24, while the second bank 26 can include a number of radially arranged columns 28. The columns 24 can be single use columns for absorbing and reacting precursors, while the columns 28 can similarly be single use columns for purification of the products formed in the first bank 22. In one aspect, one or more of the columns 24 and the columns 28 may be substituted for or used as waste columns, cleaning columns, recover ports, empty chambers, the like, and combinations thereof. For example, the column 24a and the column 28a (or the chamber in the bank 22 or the bank 26 for containing the column 24a or the column 28a, respectively) may be used to for collecting waste material or for flowing waste material through the module 20. Further, the second bank 26 can be designed to accommodate a thermocouple (not shown) in a thermocouple slot 66 or a heating cartridge (not shown) for controlling the temperature of the columns 28 in a heating cartridge slot 68.

Figure 11A:
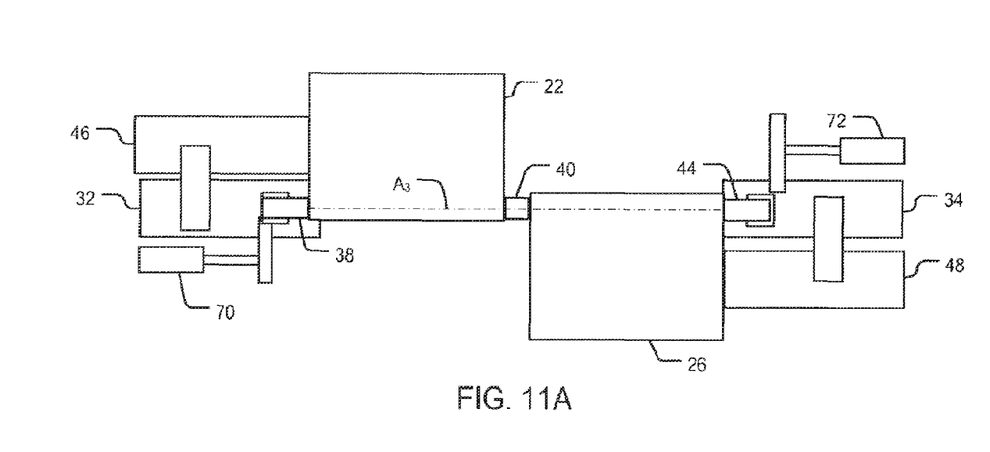
FIG. 11A is another schematic illustration of the example system of FIG. 5A showing the system in a first, fully coupled state where a continuous fluid path extends from the reagent delivery valve to the output selector valve.
Figure 11B:
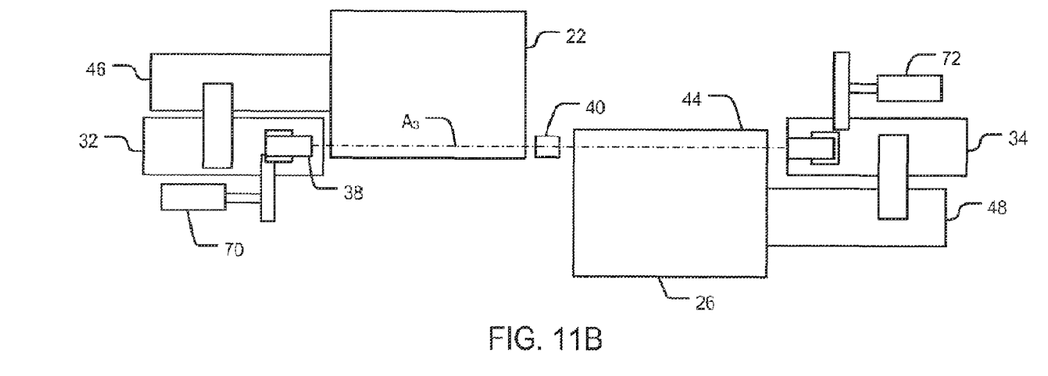
FIG. 11B is a schematic illustration similar to FIG. 11A showing the system in a second, fully separated state where the fluid path between the reagent delivery valve and the output selector valve is disrupted such that the first bank and the second bank may be independently rotated about a corresponding axis of rotation.

Turning now to FIGS. 11A and 11B, a first linear actuator 70 is operable to slide or translate the at least one of the fitting 38, the first bank 22, and the intermediate fitting 40 along a path that is parallel to the axis A$_3$. In another aspect, a second linear actuator 72 is operable to slide or translate at least one of the fitting 44, the second bank 26, and the intermediate fitting 40 along an axis parallel to the axis A$_3$. In one embodiment, the intermediate fitting 40 may be held in a fixed position, while the first linear actuator 70 may be coupled to the fitting 38 and the first bank 22, and the second linear actuator 72 may be coupled to the fitting 44 and the second bank 26. Operation of the first linear actuator 70 may guide (pull) the first bank 22 away from the intermediate fitting 40, thereby disconnecting the first bank 22 from the intermediate fitting 40. Subsequently, the first linear actuator 70 may guide (pull) the fitting 38 away from the first bank 22, thereby disconnecting the first bank 22 from the fitting 38. In one aspect, stops (not shown) may be include to prevent the continued translation of the first bank 22 in order to disconnect the first bank 22 from the fitting 38. Similarly, operation of the second linear actuator 72 may guide (pull) the second bank 26 away from the intermediate fitting 40, thereby disconnecting the second bank 22 from the intermediate fitting 40. Subsequently, the second linear actuator 72 may guide (pull) the fitting 44 away from the second bank 26, thereby disconnecting the second bank 26 from the fitting 44. Stops (not shown) may be included to prevent the continued translation of the second bank 26 in order to disconnect the second bank 26 from the fitting 44.

In one example, purified $^{18}$F—AcF was trapped in anhydrous polar organic solvents such as acetonitrile, or on solid-phase extraction cartridges such as Oasis WAX, or in a cooled tubing loop at −40° C. to −80° C. An acetone rinse cycle was used between runs. $^{18}$F—AcF was produced in decay-corrected radiochemical yields of 93.3±5.3% in 20-25 min. Further reductions of production time are anticipated. Radiochemical purity was >99% by radio-GC. Radiochemical stability of $^{18}$F—AcF was >99% to at least 4 h post-production. $^{18}$F—AcF was readily transported in nitrogen through 15 m of 0.8 mm ID polypropylene tubing with low (0.64±0.12%) adsorption to the tubing. Following dissolution of $^{18}$F—AcF in acetonitrile containing the phase-transfer catalyst tetraethylammonium bicarbonate and various labeling precursors, both aliphatic and aryl radiofluorinations were achieved in medium to high yields. After measurement of the limit of detection for AcF, the specific activity was estimated to be >1.3 GBq/umol with a starting radioactivity of 1.5 GBq.

$^{18}$F-acyl fluorides represent a new paradigm for preparation and transport of anhydrous, reactive $^{18}$F-fluoride as raw material for radiofluorinations. The automated module opens the possibility for production of highly transportable $^{18}$F-acyl fluorides near to the cyclotron and highly efficient transport of $^{18}$F-fluoride in the gas phase. Furthermore, this overcomes limitations imposed by transport of $^{18}$F-fluoride in water and the required maintenance of the isotope delivery lines.

The present invention has been described in terms of one or more preferred embodiments, and it should be appreciated that many equivalents, alternatives, variations, and modifications, aside from those expressly stated, are possible and within the scope of the invention.

Each reference identified in the present application is herein incorporated by reference in its entirety.

While present inventive concepts have been described with reference to particular embodiments, those of ordinary skill in the art will appreciate that various substitutions and/or other alterations may be made to the embodiments without departing from the spirit of present inventive concepts. Accordingly, the foregoing description is meant to be exemplary, and does not limit the scope of present inventive concepts.

A number of examples have been described herein. Nevertheless, it should be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the present inventive concepts.

INDUSTRIAL APPLICABILITY

The invention relates to the manufacture of radiopharmaceuticals and particularly, the manufacture of $^{18}$F-containing PET tracers for clinical use using gaseous $^{18}$F-compounds instead of aqueous [$^{18}$F]fluoride as the source of the $^{18}$F-label.

The invention claimed is:

1. A method for preparing a gaseous $^{18}$F-compound for labeling a positron emission tomography (PET) tracer precursor compound with $^{18}$F, the method comprising:
contacting a composition comprising [$^{18}$F]fluoride ions with an anhydride having the formula:

wherein each R is independently a halogen substituted or an unsubstituted, straight chain or branched $C_1$-$C_4$ alkyl group, wherein the composition comprising the [$^{18}$F]fluoride ions comprises an ion-exchange resin on which the [$^{18}$F]fluoride ions are trapped;
whereby a gaseous $^{18}$F-compound is produced having the formula:

2. The method of claim 1, wherein the gaseous $^{18}$F-compound is anhydrous.

3. The method of claim 1, wherein the step of contacting the composition comprising [$^{18}$F]fluoride ions with the anhydride occurs at a temperature of 50-70° Celsius.

4. The method of claim 1, wherein R is an alkyl group that is substituted with one or more halogen atoms.

5. The method of claim 4, wherein the one or more halogen atoms are selected from the group consisting of fluorine and chlorine.

6. The method of claim 5, wherein R is selected from the group consisting of —$CH_2F$, —$CH_2Cl$, and —$CHFCH_3$.

7. The method of claim 1, wherein R is selected from the group consisting of —$CH_3$, and —$CH_2CH_3$.

8. The method of claim 7, wherein R is —$CH_3$.

9. The method of claim 1, wherein the composition comprising the [$^{18}$F]fluoride ions comprises an anion-exchange resin on which the [$^{18}$F]fluoride ions are trapped.

10. The method of claim 9, wherein the composition comprising [$^{18}$F]fluoride ions trapped on the anion-exchange resin is produced by contacting the anion-exchange resin with a water solution comprising [$^{18}$F]fluoride ions and subsequently drying the resin.

11. The method of claim 10, wherein the resin is dried by rinsing the resin with acetone, followed by exposing the resin to a flow of nitrogen gas.

12. The method of claim 9, wherein the anion exchange resin is a weakly basic, macroporous anion exchange resin having beads of uniform size.

13. The method of claim 12, wherein the anion exchange resin comprises a styrene-divinylbenzene copolymer matrix and tertiary and quaternary ammonium groups.

14. The method of claim 13, wherein the anion exchange resin is a carbonate form resin.

15. The method of claim 10, wherein the water solution comprising [$^{18}$F]fluoride ions is produced by contacting one or more accelerated protons with $^{18}$O-enriched target water.

16. The method of claim 15, wherein the step of contacting one or more accelerated protons with the $^{18}$O-enriched target water is performed in close proximity to the step of contacting the composition comprising [$^{18}$F]fluoride ions trapped on the anion-exchange resin with the anhydride to produce the gaseous $^{18}$F-compound.

17. The method of claim 16, wherein the step of contacting one or more accelerated protons with the $^{18}$O-enriched target water is performed within fifteen feet of the step of contacting the composition comprising [$^{18}$F]fluoride ions trapped on the anion-exchange resin with the anhydride to produce the gaseous $^{18}$F-compound.

18. The method of claim 16, wherein the steps of contacting one or more accelerated protons with the $^{18}$O-enriched target water and contacting the composition comprising [$^{18}$F]fluoride ions trapped on the anion-exchange resin with the anhydride to produce the gaseous $^{18}$F-compound are both performed within a cyclotron vault.

19. The method of claim 18, wherein the gaseous $^{18}$F-compound is stored within the cyclotron vault.

20. The method of claim 1, wherein the gaseous $^{18}$F-compound is reacted with a precursor in a microfluidic device.

21. The method of claim 1, wherein the gaseous $^{18}$F-compound is transported to a radiochemistry hot cell.

22. The method of claim 21, wherein the gaseous $^{18}$F-compound is transported to the radiochemistry hot cell via polymeric tubing.

23. The method of claim 1, further comprising the step of contacting the gaseous $^{18}$F-compound with a PET tracer precursor compound, whereby the PET tracer precursor compound is labeled with $^{18}$F to produce an $^{18}$F-labeled PET tracer compound.

24. The method of claim 23, wherein the $^{18}$F-labeled PET tracer compound produced is [$^{18}$F]2-fluoro-2-deoxyglucose (FDG) or [$^{18}$F]tetraflouroborate ($BF_4^-$).

25. The method of claim 1, further comprising the step of contacting the gaseous $^{18}$F-compound with a composition comprising an organic solvent, whereby the gaseous $^{18}$F-compound is trapped within the composition.

26. The method of claim 25, wherein the organic solvent is acetonitrile.

27. The method of claim 25, wherein the composition comprising the organic solvent further comprises a phase transfer catalyst, a PET tracer precursor compound, or both.

28. The method of claim 27, wherein the phase transfer catalyst is tetraethylammonium bicarbonate, tetrabutylammonium bicarbonate, cesium carbonate, or cesium bicarbonate.

29. The method of claim 1, further comprising the step of contacting the gaseous $^{18}$F-compound with a second gas to form an $^{18}$F-labeled radioactive product.

30. The method of claim 29, wherein the second gas is $BF_3$, and wherein the $^{18}$F-labeled radioactive product is [$^{18}$F]$BF_4^-$.

* * * * *